United States Patent [19]

Jenks

[11] Patent Number: 4,931,731
[45] Date of Patent: Jun. 5, 1990

[54] MAGNETIC PARTICLE INSPECTION APPARATUS WITH ENHANCED UNIFORMITY OF MAGNETIZATION

[76] Inventor: William C. Jenks, 5225 Sapphire Ave., Alta Loma, Calif. 91701

[21] Appl. No.: 349,972

[22] Filed: May 8, 1989

Related U.S. Application Data

[63] Continuation of Ser. No. 141,071, Jan. 5, 1988, abandoned.

[51] Int. Cl.$^5$ ...................... G01N 27/84; G01R 33/12
[52] U.S. Cl. .................................... 324/216; 324/232; 324/262
[58] Field of Search ............... 324/214, 215, 216, 226, 324/227, 228, 232, 234, 238, 262, 263; 361/143

[56] References Cited

U.S. PATENT DOCUMENTS

| | | | |
|---|---|---|---|
| 2,110,759 | 3/1938 | De Forest | 324/263 |
| 2,242,366 | 5/1941 | Muller | 175/183 |
| 2,423,552 | 7/1947 | Clarke | 175/183 |
| 2,481,937 | 9/1949 | Mages | 175/335 |
| 3,034,021 | 5/1962 | Callihan | 317/123 |
| 3,324,354 | 6/1967 | Schroeder et al. | 361/143 |
| 3,694,740 | 9/1972 | Bergstrand | 324/37 |
| 4,443,759 | 4/1984 | Isaacson et al. | 324/216 |

*Primary Examiner*—Reinhard J. Eisenzopf
*Assistant Examiner*—Walter E. Snow
*Attorney, Agent, or Firm*—Harvey S. Hertz

[57] ABSTRACT

A ferrous metal inspection device particularly for elongated parts provides high intensity DC magnetic fields in each of two modes contemporaneously. One mode is generated by passing a DC current axially through the part to be inspected and the other is generated by a separate DC current passing through a pair of electromagnet coils positioned one at each axial end of a part to be inspected. Magnetic field lines are thereby generated in a pair of mutually orthogonal planes. Control and polarity of the two direct currents is effected by controlling the phase of conduction of separate corresponding silicon controlled rectifiers. The part to be inspected is drenched with a mixture of fine ferrous particles in a liquid vehicle. Solenoid wound coils connected in series or parallel are placed, one at each end of the part and a third coil surrounds the part circumferentially, thereby producing two substantially orthogonal magnetic fields. The ferrous particles of any orientation define flaws in the part being tested, for visual evaluation.

11 Claims, 2 Drawing Sheets

MAGNETIC PARTICLE INSPECTION APPARATUS WITH ENHANCED UNIFORMITY OF MAGNETIZATION

This is a continuation of co-pending application Ser. No. 07/141,071 filed on Jan. 5, 1988 now abandoned.

BACKGROUND OF THE INVENTION

1. Field of the Invention

The invention relates generally to quality control inspection of ferrous metal parts and more particularly to wet particle systems in which fine ferrous particles in oil are bathed onto the part for flaw detection.

(2) Description of the Prior Art

In the prior art, the basic technique of detecting faults or cracks (flaws) in a manufactured ferrous metal part by magnetizing the part and bathing it in a slurry of fine particles of iron in a vehicle of oil. The faults or flaws tend to be visually observable in that they form a characteristic interruption of the otherwise uniform pattern of the iron particles (filings) clinging magnetically to the magnetized part. That technique has sometimes been referred to as wet magnetic particle inspection.

As a general rule, the detection of discontinuities in ferrous materials is accomplished by generating a suitable magnetic field normal to the effected direction of the discontinuity.

U.S. Pat. No. 2,242,366 disclosed a relatively early system for dealing with the drawbacks of still earlier systems which could not detect longitudinal cracks parallel to the axis of an elongated part being inspected when the magnetization is axially applied. Similarly, transverse cracks are not detectable when the magnetization is of the circular type, such as produced by axial current flow in the part itself. In the aforementioned U.S. Pat. No. 2,212,366 (Muller) a system is disclosed in which at least one of the fields is generated by an AC current component producing an "oscillating" net field. Although workable, this system has been found to be wanting because of AC field cancellation effects under certain conditions. Moreover, any system applying a high intensity magnetic field in the longitudinal direction of the part is subject to eddy current effects which set up magnetic anomalies and can also cause heating of the part.

For locating discontinuities (cracks) at various angles on the surface of a part or within its interior, it is necessary to generate both circular and longitudinal magnetic fields. The circular field is generated by passing a current axially through the part if it is generally of cylindrical or annular cross-section, or in case of a hollow part, such as a gun barrel, a longitudinal wire within the hollow volume can also be used to generate the circular field. A longitudinal magnetic field has usually been generated in prior art devices by a loop-type electromagnet having continuous, windings in planes generally normal to the axis of the part.

Another example of a prior art system for the purpose is disclosed in U.S. Pat. No. 3,034,021 (Callihan). In that system the currents for both the axial current through the part (for circular field generation) and through a single peripheral (loop-type) electromagnet coil are supplied in parallel. Thus, individual control of those currents is not possible.

In U.S. Pat. No. 2,242,366 (Muller) aforementioned, the two magnetizing currents are likewise not individually controllable.

Various prior art arrangements using saturable reactors with selenium rectifier stacks are known in variations of the basic prior art systems. More recently, silicon diodes replaced selenium stacks for high-efficiency, smaller size and lower cost in the power supply configurations.

U.S. Pat. No. 4,443,759 (Isaacson et al) discloses the use of SCR elements in a still more recent version of an apparatus for the purpose. Thus, the concept of controlling the relatively large magnetizing currents by "firing phasing" in SCR elements is known. However, again the concept of separate control of the two components of magnetizing current escaped recognition. Still further, uniformity of magnetization in the longitudinal direction is considerably less effective in single magnetizing coil configurations. U.S. Pat. No. 4,443,759 falls in that category. The same is true of the Callihan and Muller systems discussed hereabove.

AC magnetizing current arrangements are known, but generally perform less well than contemporaneous DC systems.

The manner in which the system according to the invention deals with prior art disadvantages and shortcomings will be evident as this specification proceeds.

SUMMARY OF THE INVENTION

It may be said to have been the general object of the invention to develop a magnetic inspection system providing improved uniformity and adjustability of magnetization of a part to be inspected, thereby enhancing the detectability of the discontinuities (cracks or faults) in a ferrous metal part.

Separately controllable DC current circuits are provided so that adjustment of the balance between the corresponding two magnetic fields can be accomplished. Such adjustment is very important in realizing the uniformity of magnetization needed to accomplish the objective.

Some prior art systems have seemed to avoid the contemporaneous energization of the two fields using DC currents. However, in connection with the system of the invention, such an arrangement has proven to be effective in view of the aforementioned magnetizing current control and the use of dual (one at each end of the part to be inspected) electromagnet. The latter feature of the combination according to the invention is also very significant in achieving optimum uniform magnetization.

A unique adjustment procedure for set-up and use of the apparatus according to the invention is hereinafter described.

A detailed description of a representative embodiment according to the invention follows.

DETAILED DESCRIPTION

Figure 1:
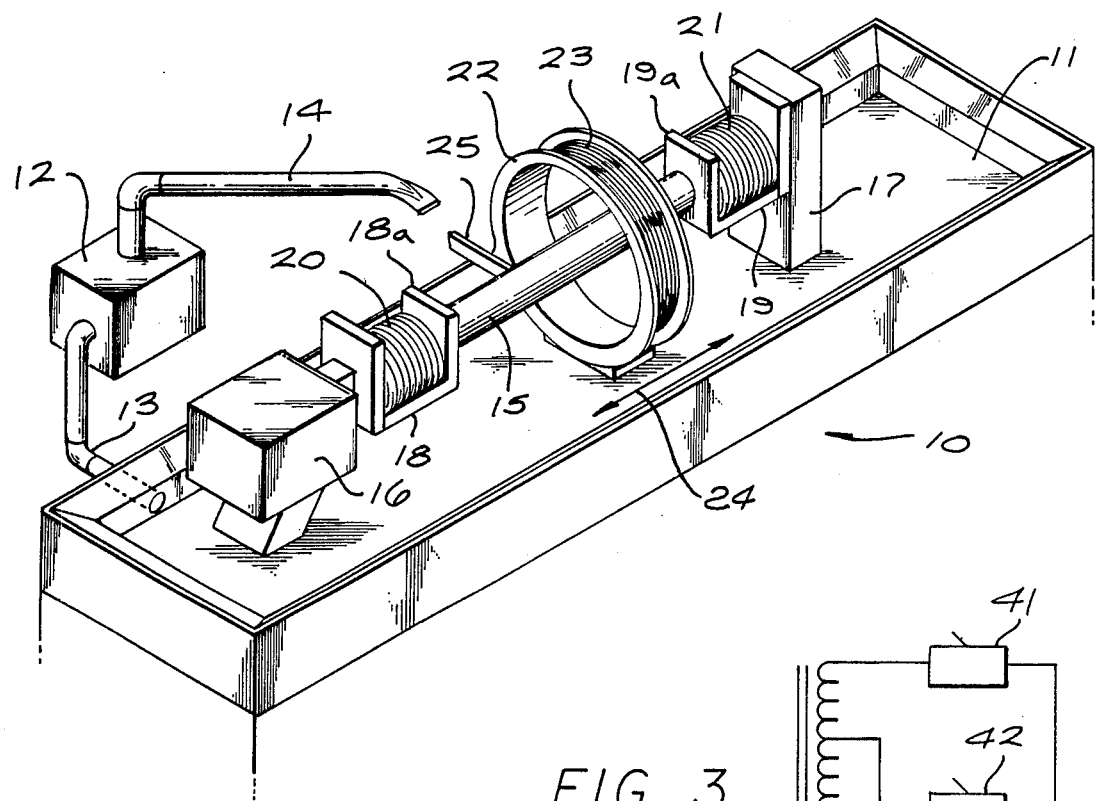
FIG. 1 is a simplified perspective view of apparatus according to the invention.

Referring now to FIG. 1, the apparatus 10 according to the invention will be seen to include an oil slurry pan 11 and a pump 12 for recirculation of the oil/iron particle slurry. Return line 13 picks up the slurry collected in pan 11 and discharges it through a spout 14 over the elongated part to be inspected 15. It will be realized that this representation is illustrative only, a more elaborate discharge nozzle being preferable at spout 14. Such an arrangement would be known in the art and it is, therefore, not necessary to provide more description of this structure.

Supports 16 and 17 are conventional per se. The support structure 16 may include a motorized axial tail stock mechanism facilitate rapid installation and removal of parts to be tested.

Coil assemblies 18 and 19 are supported within conductive cradles 18a and 19a, respectively. Preferably, these headstock parts 18a and 19a are copper, since they conduct the heavy currents passed axially through the part 15. The portions of cradles 18 and 19 (18a and 19a) abutting part 15 serve as mechanical compression member driven by an air cylinder, for example, within enclosure 16. To insure good contact, the current magnitude flowing axially through part 15 being large (several thousand amperes, typically). That current will be seen to generate the circular field.

Figure 2:
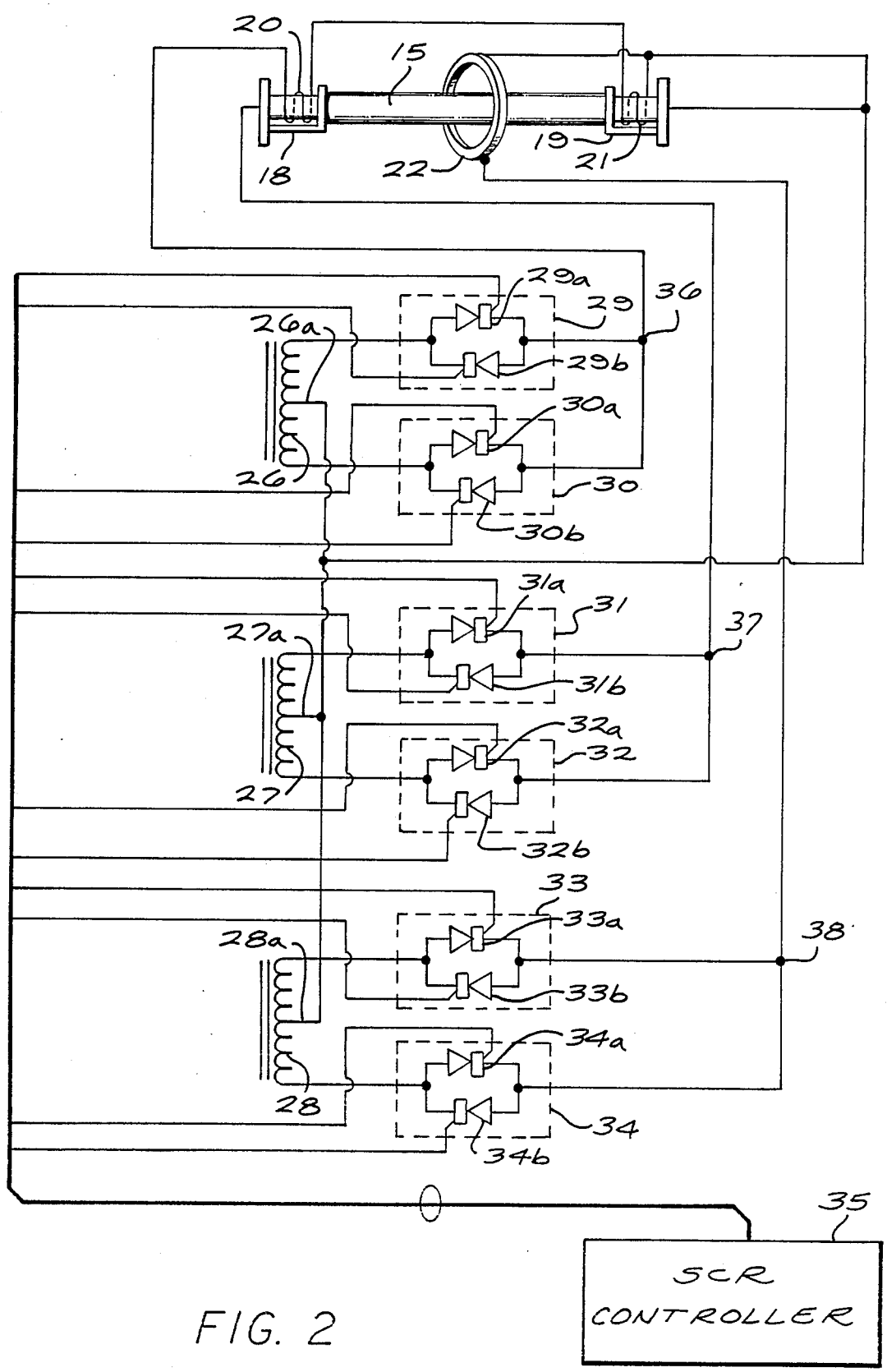
FIG. 2 is a simplified circuit diagram for the device of FIG. 1.

The electromagnet assemblies 18 and 19 will be understood to have relatively few turns of heavy gauge wire 20 and 21, solenoid wound as depicted in FIG. 1 and FIG. 2, since the current magnitude therein is similarly large. Iron cores are present within each assembly 18 and 19, but are concealed by windings 20 and 21, and may be thought of as extensions of the part 15. Such cores are conventional and may be laminated but are not necessarily so because the currents extant are pulsating DC except possibly during a demagnetizing cycle to be described later.

Whenever the part 15 is longer than thirty inches (approximately), auxiliary longitudinal magnetization may be required. For this, at least one auxillary air core, loop-type electromagnet 22 may be required. Here again, few turns (solenoid-wound) are employed as indicated at 23. The assembly 22 is axially positional as indicated by arrow 24. Windings 20, 21 and 22 are to be understood to be covered for protection with suitable insulating material, although they are illustrated without such covering for a clear understanding of their form.

Strap 25 is one of two heavy leads for carrying the large current in coil 22.

Actually, more than one auxiliary electromagnet 22 may be employed for inspection of very long parts, although parts up to 120 inches in length have been effectively inspected using the configuration of FIG. 1 (one auxiliary electromagnet 22).

Referring now to FIG. 2, the current generation and control configuration is illustrated in single phase, full wave form. Three transformer secondaries 26, 27 and 28 are shown with center taps 26a, 27a and 28a, respectively. Six SCR elements (modules) 29, 30, 31, 32, 33 and 34 are shown. Each such element comprises a pair of back-to-back SCR components, such as 29a and 29b, typically. The term back-to-back means paralleled, anode of one SCR component to cathode of the other as shown in FIG. 2.

The electromagnets 18 and 19 have their windings 20 and 21 connected in series as shown. Accordingly, the same current passes through both of those coils, providing economy of high current circuitry and also improved uniformity of longitudinal magnetization of the part 15.

The circuits including transformer secondary 26 and SCR elements (modules) 29 and 30 form a familiar full wave rectifier configuration. When SCR components 29a and 30a are controlled to be conductive by controller 35, the output DC at point 36 is positive and a current path through windings 20 and 21 back to transformer center tap 26a is established. Similarly, from point 37 the axial current through part 15, as previously described, flows back to transformer center tap 27a. Point 37 is also positive in polarity when SCR components 31a and 32a are controlled to conduct by SCR control signals from 35.

The same applies to point 38 from which current flows through the auxiliary electromagnet loop 22 back to transformer center tap 28a when SCR components 33a and 34a are in the conductive mode.

Points 36, 37 and 38 become negative when the other SCR components, i.e. 29b, 30b, 31b, 32b and 34b are controlled into conduction from controller 35.

While some high current DC rectification systems employ half-wave rectification, the full-wave configuration, whether positive or negative in output, is more efficient and economical of AC line current demand.

The controller 35 is to be understood to contain the circuitry (conventional per se) for varying the phase angle of SCR conduction to smoothly control currents delivered at points 36, 37 and 38. This concept is described in U.S. Pat. No. 4,238,723 of inventorship in common with the present inventor as herein described.

Thus, all magnetization currents can be adjusted for optimum system performance, this being of great importance in providing the advantages of the invention. In view of the current control aspect of the combination of the invention, it will be realized by the skilled reader that multiple functions are inherent in the system. The auxiliary loop electromagnet 22 is usually not needed for operation with shorter parts, consequently the controller 35 can be set to omit any firing signals to the SCR components of SCR elements (modules) 33 and 34. All rectifier assemblies providing current from points 36, 37 and 38 are likewise capable of both positive and negative polarities, AC output (when all SCRs are enabled), and current magnitude control through SCR conduction phase control from controller 35. Still further, downward programming of current magnitudes is provided in controller 35 which gradually reduces the phase angle of SCR conduction substantially to zero while introducing either AC output or alternating DC outputs to effect demagnetization of the part being inspected. Demagnetization is sometimes very important as residual magnetism can interfere with a part's function in some mechanisms.

Figure 3:
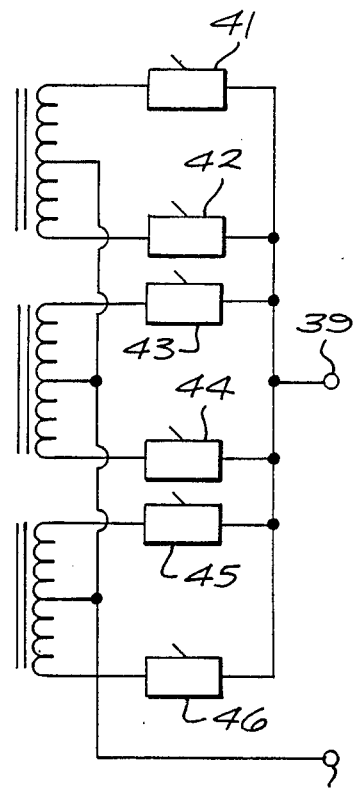
FIG. 3 illustrates the use of a three phase AC power source in each of the three rectifier circuits of FIG. 2.

FIG. 3 illustrates a three phase power supply configuration in lieu of the basically separate phase FIG. 2 arrangement. The circuit of FIG. 3 would replace each transformer secondary and SCR combinations from FIG. 1 and typically could be rectifier elements 41–46 comprising three full wave rectifier circuits. That is, the FIG. 3 circuits providing the output between terminals 39 and 40 would replace each of the three circuit subassemblies of FIG. 1 such as transformer secondary 26 and SCR elements 29 and 30, for example. The advantage achieved by a three phase configuration is economy of AC line loading and smaller conductor sizes at key AC points in the circuit. The advantage is akin to that achieved by the well-known four wire star three phase configuration of power circuits. It will be evident that the arrangement of FIG. 1 may result in unequal locking of the three phases of the power source, since each of the circuits providing the pulsating currents at points 36, 37 and 38 operates as a single phase circuit of itself. However, that fact is of no consequences operationally. It will also be realized that because of the three phase power for the FIG. 2 source that there will be an inherent phase shift among the pulsating DC waves at points 36, 37 and 38.

Figure 4:
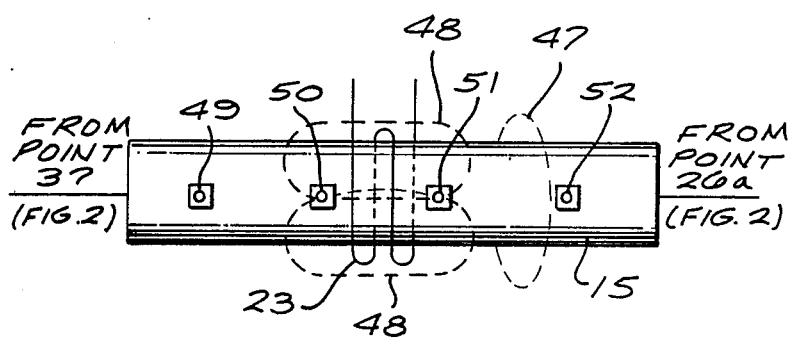
FIG. 4 illustrates the formation of the two orthogonal magnetic fields according to the invention and shows additional structure (artificial flaw shims) implementing a set-up and operating procedure.

Referring now to FIG. 4, the relationship between the circular magnetic field 47 and the longitudinal field 48 is illustrated. The main longitudinal magnetization structure including coil assemblies 18 and 19 are not shown. However, auxiliary electromagnet winding 23 is shown. The longitudinal field generation of loop electromagnet 22 is analogous to that of the main magnetization assemblies 18 and 19, and the illustration of FIG. 4 is selected to more easily depict the two contemporaneous DC fields employed.

In FIG. 4, the inclusion of a plurality of artificial flaw shims placed on part 15 using a pressure sensitive adhesive or tape is shown. These artificial flaw shims are an article of commerce and are offered as Quantitative Quality Indicator (QQI chips) by Kermit Skeie Associates, 3238 Belle River Drive. Hacienda Heights, CA 91745.

The so-called QQI chips are thin pure iron shims on the order of 0.002 to 0.004 inches thick and approximately three-fourths of an inch square with a circular artificial flaw milled into the chip thickness to a depth between 15% and 60% of the chip's thickness. Using these chips placed at various points on the perimeter of the part to be inspected, adjustments of magnetization currents (and consequently resulting fluxes) can be undertaken to ensure uniform flux density. Accordingly, visual observation confirms proper adjustment of currents.

Figure 5A:
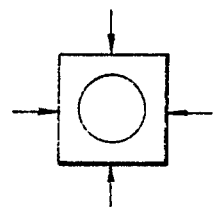
FIG. 5a illustrates the visual pattern provided by the artificial flaw shims with uniform magnetization balance between circular and longitudinal magnetic flux intensities.
Figure 5B:
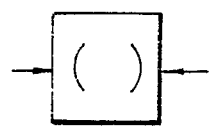
FIG. 5b and 5c illustrates the visual artificial flaw pattern resulting from only longitudinal and circular mode magnetization, respectively.
Figure 5C:
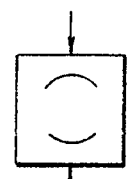

FIG. 5a depicts the visual response of the artificial flaw when uniform magnetization in both coordinates is extant. FIG. 5b depicts the QQI appearance when only the longitudinal field is detected, and FIG. 5c depicts the appearance when only the circular field is detected. The foregoing, of course, assumes that the part surface is bathed in the iron filing/oil slurry used in actual flaw detection. Removal of the QQI chips is recommended once the current adjustments have been made, before proceeding with inspection of further samples of the same part.

Modifications and variations falling within the spirit of the invention will suggest themselves to those of skill in this art. For one such variation, it will be realized that electromagnet loop coils such as 22 could be substituted for assemblies 18 and 19.

In some instances an AC field in one of the magnetization directions may be desirable with a DC field in the other component of magnetization. In view of the capability of the invention combination, the flexibility to accomplish such an alternate magnetization program is available as previously described. Moreover, for demagnetization, AC fields or reversing DC fields can be employed by appropriate control of SCR enablement.

Still further, although the electromagnets 18 and 19 (FIG. 2) are shown with their windings 20 and 21 respectively, electrically in series, they could also obviously be connected in parallel although the total current required from point 36 would thereby be doubled. Since magnetic field intensities (flux densities) are a direct function of electromagnet current the same current can be employed more economically in the series configuration of FIG. 2.

Finally, although it is conventional to employ an oil as the carrier for the iron particles bathed onto the part being inspected, the oil is only a non-reactive vehicle and accordingly other liquids, even water, could be substituted.

Accordingly, it is not intended that the scope of the invention should be regarded as limited by the specifics of the drawings on this description, these being intended to be typical and illustrative only.

I claim:

1. A magnetic inspection system for detecting flaws in ferrous metal parts, comprising:

first means for passing a first pulsating direct current axially through a part to be inspected thereby generating a corresponding first magnetic field associated with said part;

second means for generating a second magnetic field generally orthogonal with respect to said first magnetic field, said second means including a pair of solenoid-wound first electromagnets adjacent to said part to be inspected, one of said first electromagnets being adjacent at each end of said part. said first electromagnets being energized by a second pulsating direct current;

third means comprising circuits connected from a three-phase alternating current source for supplying said first and second pulsating direct circuits. from first and second phases of said three-phase source, respectively, the pulses of said first and second direct currents being phase displaced from each other because of the inherent phase relationship among the phases of said alternating current source;

fourth means associated with said third means for independently controlling the magnitudes and polarities of said first and second pulsating currents to achieve a predetermined balance between said first and second magnetic fields; and fifth means for bathing said part to be inspected in a fluid vehicle containing finely powdered magnetizable particles, thereby to exhibit a characteristic visual pattern of said particles under the influence of said magnetic fields at the location of any flaw in said part.

2. The system according to claim 1 in which said fourth means comprises a full wave rectifier circuit having two pairs of back-to-back solid state controlled rectifiers responsive to said phases of said three-phase source to produce said first and second pulsating currents, said fourth means also comprising controller means for determining the phase angles of conduction of said solid state controlled rectifiers in pairs of the same polarity to generate said pulsating currents at predetermined magnitudes, the remaining rectifier pairs of opposite polarity being similarly controlled to alternatively produce said first and second pulsating currents of a second polarity.

3. The system according to claim 2 in which said solid state controlled rectifiers are silicon controlled rectifiers.

4. The system according to claim 2 in which said controller is adapted to control both of said back-to-back rectifiers of a selected one of said full-wave rectifier circuits into conduction to produce an alternating current for demagnetization of said part under test.

5. The combination set forth in claim 1 in which each of said second means electromagnets has a core of magnetic material and said solenoid winding comprises a plurality of winding turns each in a plane substantially perpendicular to the axis of said part, said cores abutting the ends of said part.

6. The combination according to claim 1 in which said second means electromagnets are connected in series electrically.

7. The combination according to claim 1 further including a third solenoid-wound electromagnet of generally circular loop type mounted to be selectively positioned axially with said part passing through the interior thereof, said third electromagnet acting as a booster magnetizing source for inspection of long parts, said third means including means for generating and applying a third direct current to said third electromagnet, and said fourth means including means for independently controlling the magnitude of said third direct current contemporaneously with application of said first and second direct currents.

8. In a wet process magnetic inspection system in which an elongated magnetizable part to be inspected is bathed in a fluid vehicle carrying fine magnetizable particles and longitudinal and circular mutually orthogonal fields are applied thereto, the combination comprising:

first means including an AC power source of more than one phase, a first network of SCR elements responsive to one phase of said power source for full wave rectification of said power to provide a first pulsating DC current connected to pass axially through said part to produce said circular magnetic field about said elongated part;

second means including first and second electromagnetics positioned one adjacent each end of said elongated part to produce a net longitudinal magnetic field within said elongated part in response to current in said electromagnets;

third means including a second network of SCR elements responsive to a second phase of said AC power source for full-wave rectification thereof to provide a pulsating DC current to said second means electromagnets to generate said longitudinal magnetic field in said elongated part; and fourth means for controlling the phase angle of conduction of said SCR elements to independently control the magnitude and polarity of said pulsating DC currents produced by said first and third means to control the corresponding magnitudes of said circular and longitudinal magnetic fields extant contemporaneously but with phase offset corresponding to the phase offset between phases of said AC power source.

9. The combination according to claim 8 in which said SCR elements of said first and third means each comprise a pair of back-to-back SCR components separately controllable and said fourth means is adapted to select one of said SCR components of each SCR element pair to provide polarity reversal of said DC currents supplied by said first and third means.

10. The combination according to claim 9 in which said fourth means are controllable to program said DC current magnitudes downward to substantially zero while periodically reversing said polarization, to effect demagnetization of said elongated part.

11. The combination set forth in claim 9 in which said second means electromagnets is a solenoid-wound electromagnet on a magnetic core, said cross abutting said elongated part, one at each end thereof.

* * * * *